US010603205B2

(12) United States Patent
Yang (10) Patent No.: US 10,603,205 B2
(45) Date of Patent: Mar. 31, 2020

(54) PORTABLE URINATION DEVICE

(76) Inventor: Kuohuang Yang, Taipei (TW)

(*) Notice: Subject to any disclaimer, the term of this patent is extended or adjusted under 35 U.S.C. 154(b) by 1012 days.

(21) Appl. No.: 13/643,843

(22) PCT Filed: Aug. 26, 2011

(86) PCT No.: PCT/CN2011/001437
§ 371 (c)(1),
(2), (4) Date: Oct. 26, 2012

(87) PCT Pub. No.: WO2012/083581
PCT Pub. Date: Jun. 28, 2012

(65) Prior Publication Data
US 2013/0263365 A1    Oct. 10, 2013

(30) Foreign Application Priority Data

Dec. 20, 2010  (CN) .......................... 2010 1 0596102

(51) Int. Cl.
*A61F 5/455*    (2006.01)
(52) U.S. Cl.
CPC .................................. *A61F 5/4556* (2013.01)
(58) Field of Classification Search
CPC .. A61F 5/4556; A61B 10/007; A61G 2200/12
USPC ............... 4/144.1–144.4, 479; 604/329, 347; 141/331, 337
See application file for complete search history.

(56) References Cited

U.S. PATENT DOCUMENTS 2,690,568 A * 10/1954 Willis ............................. 4/144.4
2,878,486 A *  3/1959 Bartlett et al. ................. 4/144.4
4,681,573 A *  7/1987 McGovern et al. ........... 604/329
4,751,751 A *  6/1988 Reno .............................. 4/144.4
5,742,948 A *  4/1998 Cicio ............................. 4/144.3
6,434,757 B1* 8/2002 Filsouf ........................... 4/144.2
2006/0218709 A1* 10/2006 Langford ....................... 4/144.4
2011/0042258 A1*  2/2011 Nett ............................. 206/494
2011/0087183 A1*  4/2011 Yang ............................. 604/347
(Continued)

FOREIGN PATENT DOCUMENTS

| CN | 1127985 A | 7/1996 |
| CN | 2668094 Y | 1/2005 |
| CN | 201244114 Y | 5/2009 |

(Continued)

*Primary Examiner* — Erin Deery
*Assistant Examiner* — William R Klotz
(74) *Attorney, Agent, or Firm* — Muncy, Geissler, Olds & Lowe, P.C.

(57) ABSTRACT

A portable urination device comprises a guiding body and two connection units. The guiding body has a guiding portion, a first port and a second port. The guiding portion is formed of two side walls, and the bottom edge of the side wall is of a closed structure. The first port and the second port are oppositely disposed and are respectively located at two ends of the guiding portion. The two connection units are respectively extended between the first port and the second port of the guiding body. The two connection units are used for the user operation, the first port is used for receiving urine of a user, and the urine is discharged from the second port through guiding of the guiding portion, or discharged from the first port after buffering of the guiding portion. The urination device is easily used, and the user is dispense with contacting the public toilet stool.

10 Claims, 8 Drawing Sheets

(56) References Cited

U.S. PATENT DOCUMENTS

2012/0210502 A1* 8/2012 Baham .................... 4/144.3
2013/0239311 A1* 9/2013 Valenti ................... 4/144.3

FOREIGN PATENT DOCUMENTS

| CN | 102048488 A | 5/2011 |
| CN | 201959036 U | 9/2011 |
| EP | 2311414 A1 | 4/2011 |
| TW | M402704 U1 | 5/2011 |

* cited by examiner

PORTABLE URINATION DEVICE

BACKGROUND

1. Technical Field

The disclosure relates to an urination device, in particular, to a portable urination device.

2. Description of Related Art

For people away from home, the most disturbing problems than how to solve the excretion problems when there without toilets. Even find a public toilet, often encounter the problem of dirty and hygienic public toilet, people often need to use a lot of toilet paper to wipe the toilet or squat toilet, or a lot of toilet paper in the toilet mat makes using public toilet. Squat on sitting on the toilet is often a result of urine splashing while dirty thigh, the case of clothing, and the other to use a lot of toilet paper also appears to be a waste of resources and not environmental. Furthermore, a lot of female users do not want to sit on the toilet because it is dirty but preferring to hold back urine for long time to cause physical illness caused a great deal of the burden, especially to the kidneys.

Therefore, it is one of the important topics that how to provide a portable urination device, which is easy to use and can allows the users do not need to contact the public toilets when in the unclean public toilets.

SUMMARY OF THE INVENTION

In view of the foregoing, for overcoming the deficiencies of the prior art, the invention is to provide a portable urination device capable of portability, easy to use, and make users guiding the urine accurately without contact with the public toilets.

To achieve the above, a portable urination device includes a guiding body and two connection units. The guiding body has a guiding portion, a first port, and a second port. The guiding portion is consisted of two side walls made by paper or plastic. The bottom edge of the two side walls is a closed structure. The first port and the second port are positioned at two ends of the guiding portion. Two ends of the side walls are substantially the open structures. The two connection units are extended on the guiding body and positioned between the first port and the second port, respectively. The two connection units are used for controlling by users. The first port is for receiving urine, and urine is guided to the second port for discharging through the guiding portion. However, the present invention can also be used in many ways, detailed later.

According to one embodiment, wherein an open structure is positioned distant from the bottom edge of the two side walls of the guiding body.

According to one embodiment, wherein the connection unit is a foldable wing extended from one of the side walls. In addition, an angle is existed between an extended line of the top edge of the two connection units and an extended line of the bottom edge of the two side walls, and the angle is an obtuse angle. The structure with the obtuse angle can conform to the body curve, so that users can easily operate the urination device.

According to one embodiment, wherein the portable urination device further comprises a receiving portion, which is positioned at the first port near the two connection units. The receiving portion is close to the excretory opening (or vulva) to receive the urine. The extended line of the top edge of the receiving portion is approximately parallel to the extended line of the bottom edge of the two side walls.

According to one embodiment, wherein the portable urination device further comprises an adhesive layer, which is disposed on at least one portion of one of the foldable wings. The adhesive layer with different viscous is used in different cases. The adhesive layer with weak viscous may be sticked to the fingers of users. The adhesive layer with strong viscous may be sticked to the other assist connection unit.

According to one embodiment, wherein an end of the foldable wing is attached to an inside or an outside of the side wall. In other words, a containing space is formed between one of the foldable wings and one of the side walls for containing the finger of users.

According to one embodiment, wherein the portable urination device further comprises at least an assist connection unit, which is attached to the foldable wing. The assist connection unit may be a ring.

According to one embodiment, wherein the portable urination device further comprises a block portion. The block portion is disposed between the bottom edge of the two side walls and the first port to ensure the urine is discharged through the second port. In another embodiment, The block portion is disposed between the bottom edge of the two side walls and the second port to ensure the urine is discharged through the first port.

According to one embodiment, wherein the portable urination device further comprises at least a structure enhanced unit, which is disposed on at least one of the two side walls, and between the first port and the second port to strong the portable urination device to ensure the portable urination device is not easily deformed during operation.

According to one embodiment, wherein the portable urination device further comprises at least a holding portion, which is extended from at least one of the two side walls near the second port for users holding to operate the urination device.

In summary, the portable urination device according to the invention is a simple structure that is easy to use and easy to carry. The portable urination device can be easily used by the fingers of the user to control its connection unit to hygienically solved using by the toilet. The outside of the bottom edge of the two side walls of the guiding body is an open structure, therefore, users can control the opening size and position of the portable urination device steady and flexibly by the connection unit extending from the side walls on both sides. Users do not need to contact the public toilets when in the unclean public toilets and can receive the urine and guide to the toilet within.

BRIEF DESCRIPTION OF THE DRAWINGS

The parts in the drawings are not necessarily drawn to scale, the emphasis instead being placed upon clearly illustrating the principles of at least one embodiment. In the drawings, like reference numerals designate corresponding parts throughout the various diagrams, and all the diagrams are schematic.

DETAILED DESCRIPTION

Reference will now be made to the drawings to describe various inventive embodiments of the present disclosure in detail, wherein like numerals refer to like elements throughout.

Figure 1:
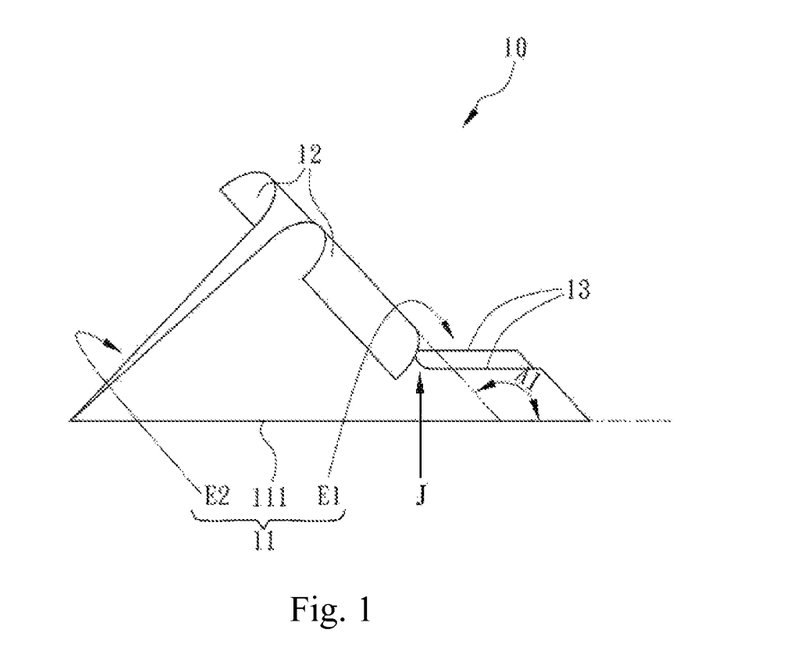
FIG. 1 is a schematic diagram showing one embodiment of a portable urination device.

Referring to FIG. 1, a portable urination device 10 is for the female user can be conveniently toileting without contacts the public toilets. One embodiment of the portable urination device 10 includes a guiding body 11 and two connection units 12. The guiding body 11 has a guiding portion 111, a first port E1, and a second port E2. The first port E1 is disposed opposite to the second port E2. The first port E1 and the second port E2 are positioned at two ends of the guiding portion 111, respectively. The connection units 12 are disposed on the guiding body 11, respectively, and are positioned between the first port E1 and the second port E2. In the embodiment, the material of the portable urination device 10 can be paper, plastic, metal, compound material, or polymer material.

The guiding portion 111 has two side walls connected to each other. The bottom edges of the two side walls are connected to each other to form a closed structure. The first port E1 and the second port E2 are positioned at two ends of a connection portion of the side walls, respectively. Two ends of the side walls, the first port E1 and the second port E2, are substantially opened. That is, an open structure is positioned distant from the bottom edge of the two side walls.

The connection units 12 can be attached to the guiding body 11 by adhering, locking, or integrated forming to provide an operating interface for users. In one embodiment, the connection unit 12 can be a foldable wing. The connection units 12 are extended distant from each side of the connection portion of the two side walls. In another embodiment, the connection unit 12 can be a ring for operating by users. An angle A1 is existed between an extended line of the top edge of the connection units 12 and an extended line of the bottom edge of the two side walls. In the embodiment, the angle A1 is an obtuse angle.

In one embodiment, the guiding body 11 further includes a receiving portion 13. The receiving portion 13 is disposed on the first port E1, which is close to the connection unit 12. The receiving portion 13 is close to or in contact with the excretory opening (or vulva) to receive the urine when using the portable urination device 10. An extended line of the top edge of the receiving portion 13 is approximately parallel to an extended line of the bottom edge of the two side walls. In other words, an obtuse angle is also existed between the extended line of the top edge of the foldable wing and the extended line of the top edge of the receiving portion 13 so that the portable urination device 10 can be ergonomic because the obtuse angle design is more close to the body curve. In the embodiment, a junction J of the foldable wing, the side wall, and the receiving portion 13 is arcuated. In using the portable urination device 10, the foldable wings, the arcuated junction J and the receiving portion 13 of the portable urination device 10 are closed to the excretory opening (or vulva) so that the urine can be guided and the urine leakage can be avoided.

Figure 2A:
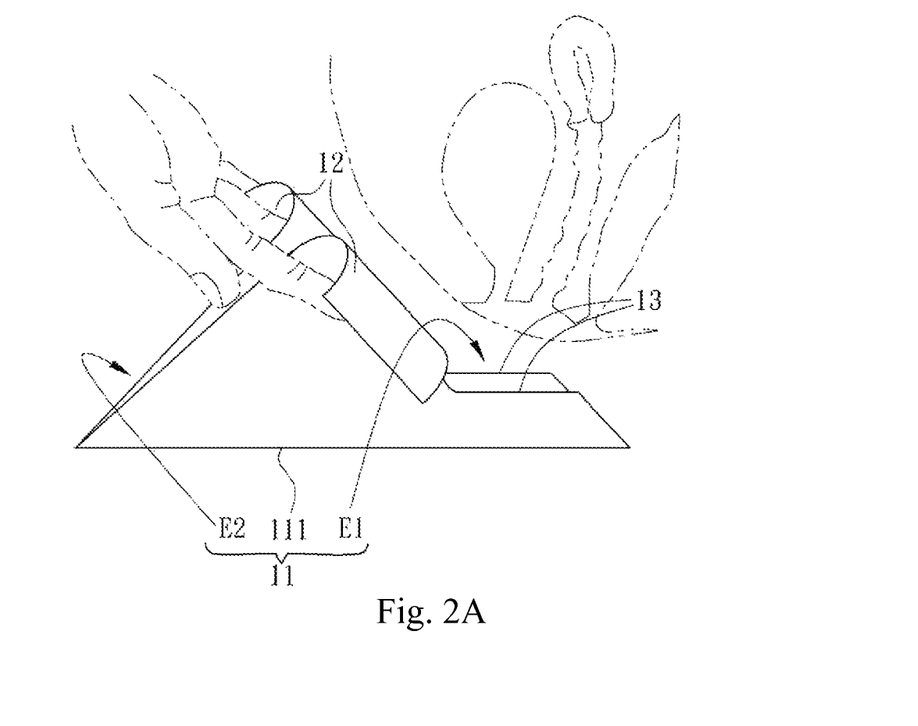
FIGS. 2A to 2C are the operating methods of the portable urination device of FIG. 1.
Figure 2B:
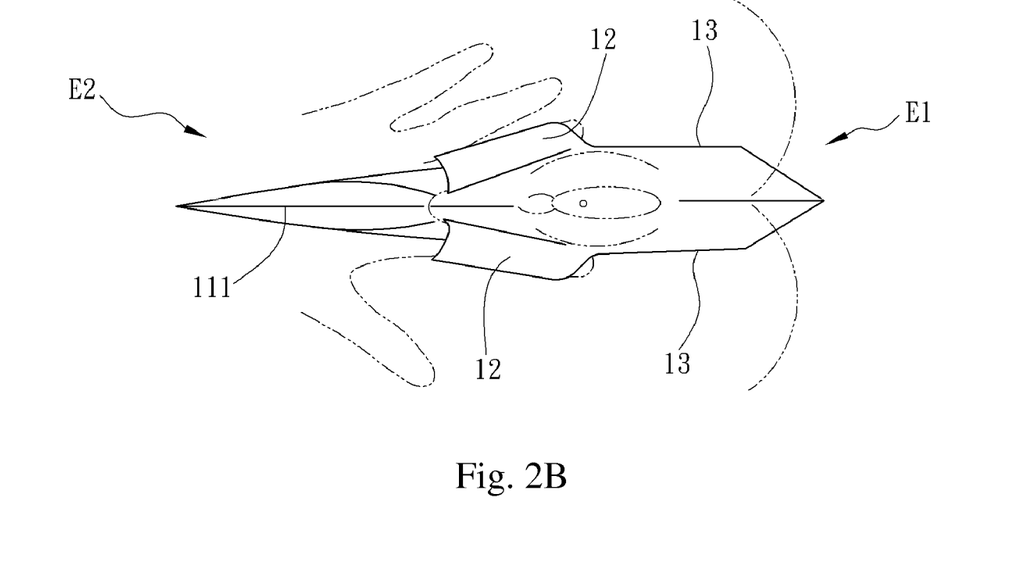
Figure 2C:
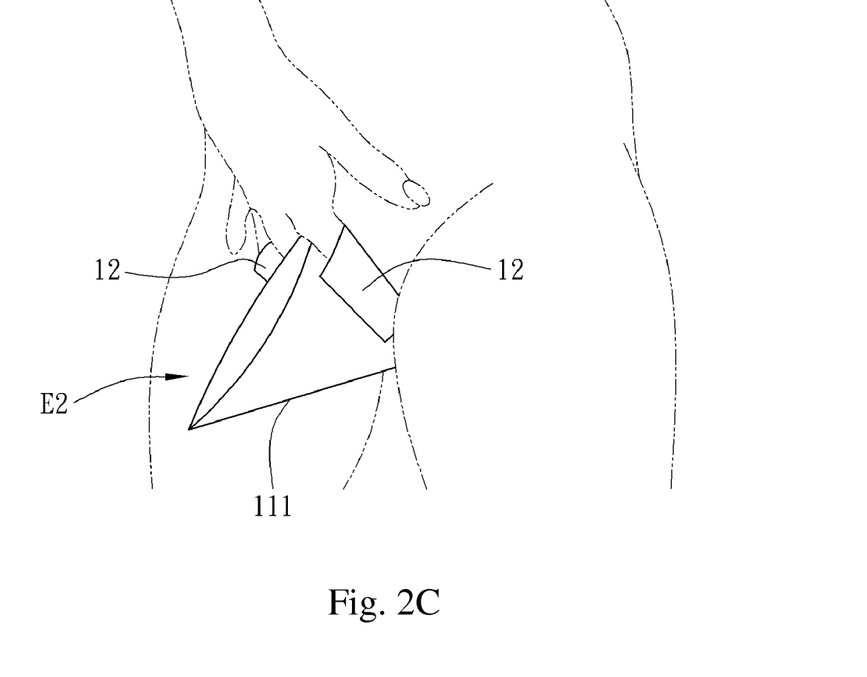

FIGS. 2A to 2C is the schematic diagrams showing the operating of the portable urination device 10. FIG. 2A is a lateral view, FIG. 2B is a top view, and FIG. 2C is a perspective view. The portable urination device 10 uses by the user that is using a finger close to the connection unit 12 to operate the portable urination device 10, so that the receiving portion 13 of the portable urination device 10 is close to the excretory opening (or vulva) of the user. The connection unit 12 closes to the pubis of the user via the two-finger control the opening size and position of the first port E1 to undertake urine, urine through the guiding portion 111 and guided to the second port E2, and discharged by the second port E2. Another operating method comprises the follow steps. In step one, urine is received by the first port E1. In step two, urine is buffered via the guiding portion 111. In step three, urine is discharged through the first port E1.

In view of above, the portable urination device 10 according to the invention is a simple structure that is easy to use and easy to carry. The portable urination device 10 can be easily used by the fingers of the user to control its connection unit 12 to guide the urine and to hygienically solve using by the toilet.

Figure 3:
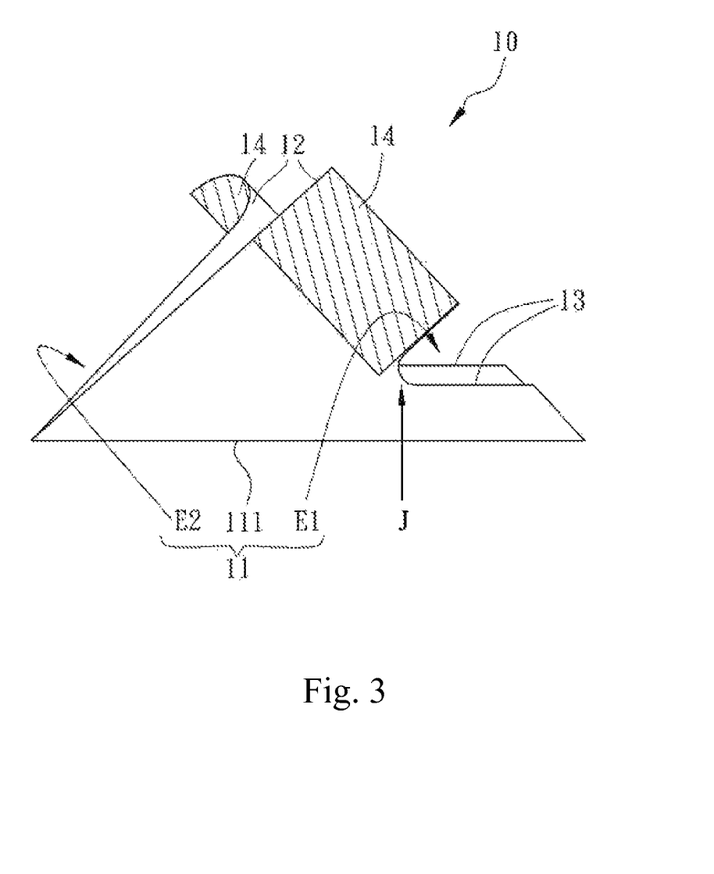
FIG. 3 is a schematic diagram showing one embodiment of the portable urination device having an adhesive layer.

Referring to FIG. 3, in another embodiment, the portable urination device 10 further includes an adhesive layer 14 disposed on the connection unit 12. The adhesive degree of the adhesive layer 14 can be variety according to diferrent operating conditions. In the embodiment, the adhesive layer 14 is an adhesive layer with weak viscous, which is disposed on the connection unit 12 (or foldable wing) near an outside of the side wall. The portable urination device 10 can be steady operated due to the finger of the user is touching to the adhesive layer 14 when operating.

Figure 10:
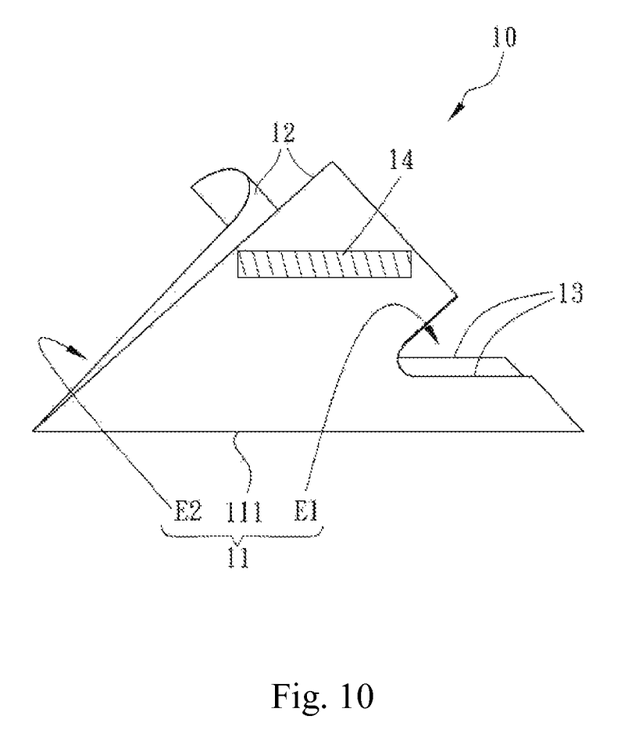
FIG. 10 is a a schematic diagram showing another embodiment of the portable urination device having a striped adhesive layer.

In another embodiment, referring to FIG. 10, the adhesive layer 14 can be disposed on a part of the connection unit 12. The striped adhesive layer 14 is approximately parallel to the extended line of the bottom edge of the two side walls. In using the portable urination device 10, two fingers of the user can touch to the striped adhesive layer 14 on the connection unit 12. Thus, the striped adhesive layer 14 can approximately surround the finger for stable operating. Moreover, the two fingers can easily separate from the striped adhesive layer 14 because the striped adhesive layer 14 and the finger is partially touched.

Figure 4A:
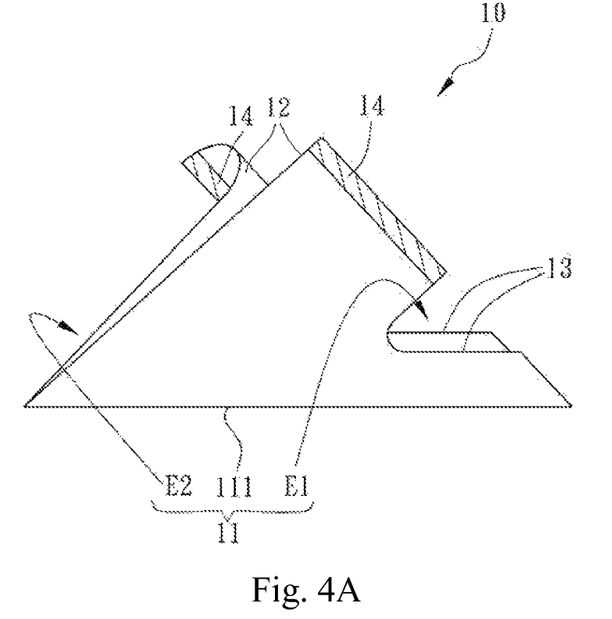
FIGS. 4A and 4B are schematic diagrams showing one embodiment of the adhesive layer is disposed on a part of the connection unit.
Figure 4B:
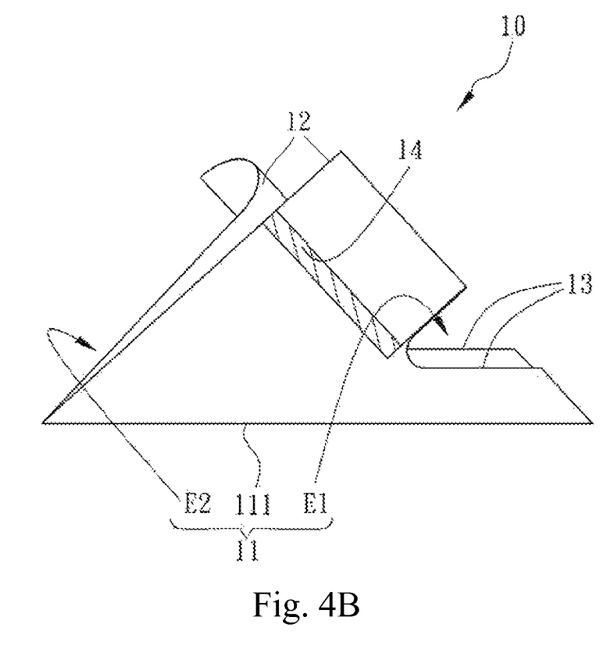
Figure 5:
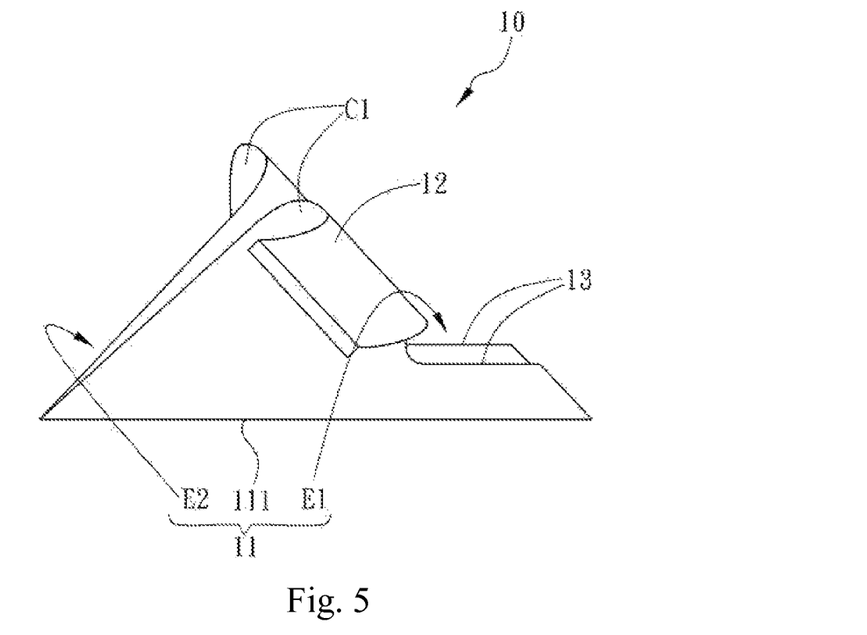
FIG. 5 is a schematic diagram showing one embodiment of a foldable wing of the portable urination device to form a containing space.

Referring to FIGS. 4A and 4B, another embodiment for the adhesive layer 14 partially disposed on the connection unit 12. The adhesive layer 14 on the connection unit 12 can be attached to the inside or the outside of the side wall, therefore, a containing space C1 (show as FIG. 5) is formed between the connection unit 12 and the side wall for supporting the finger of the user. In the embodiment, the adhesive layer 14 on the connection unit 12 is attached to the outside of the side wall (shown as FIG. 4B). The method of attaching the connection unit 12 with the side wall also can include hot pressing technique or high frequency technique.

Figure 6:
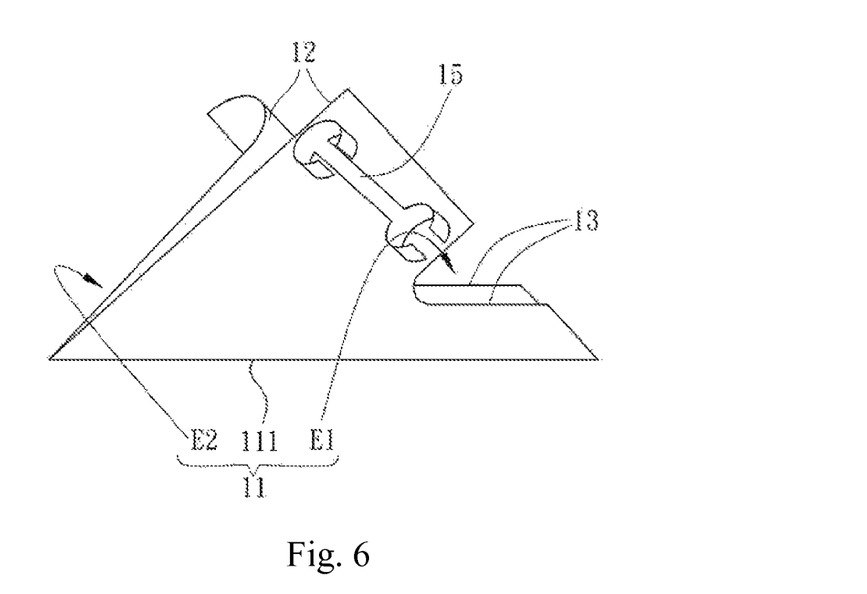
FIG. 6 is a schematic diagram showing one embodiment of the portable urination device having an assist connection unit.

Referring to FIG. 6, the adhesive layer 14 on the connection unit 12 can be attached to an assist connection unit 15 capable of fixing function, for example a ring with strong structure. The assist connection unit 15 will be beneficial to the user can be more stabilized and flexible to control the portable urination device 10. The material of the ring can be plastic or metal.

Figure 7A:
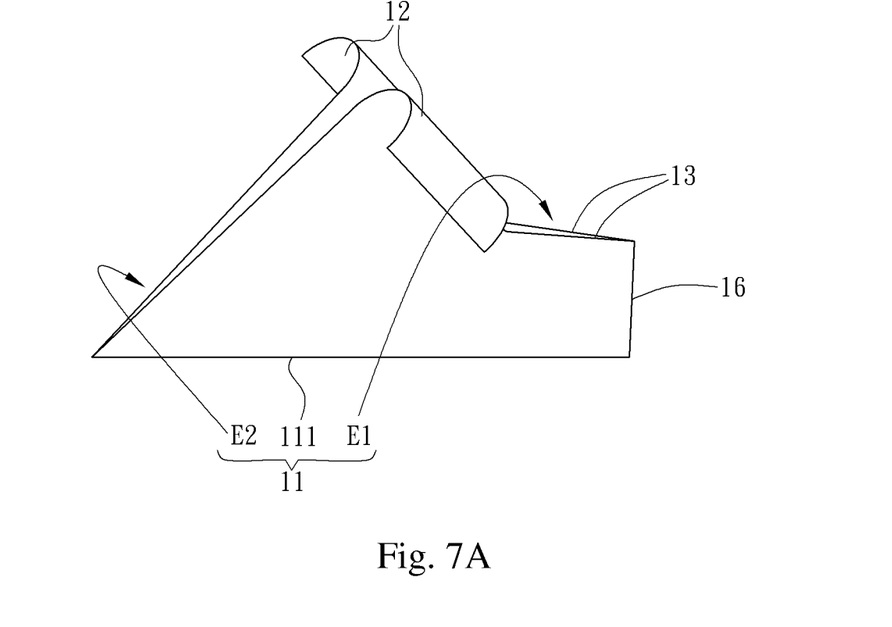
FIGS. 7A and 7B are schematic diagrams showing one embodiment of the portable urination device having a block portion.
Figure 7B:
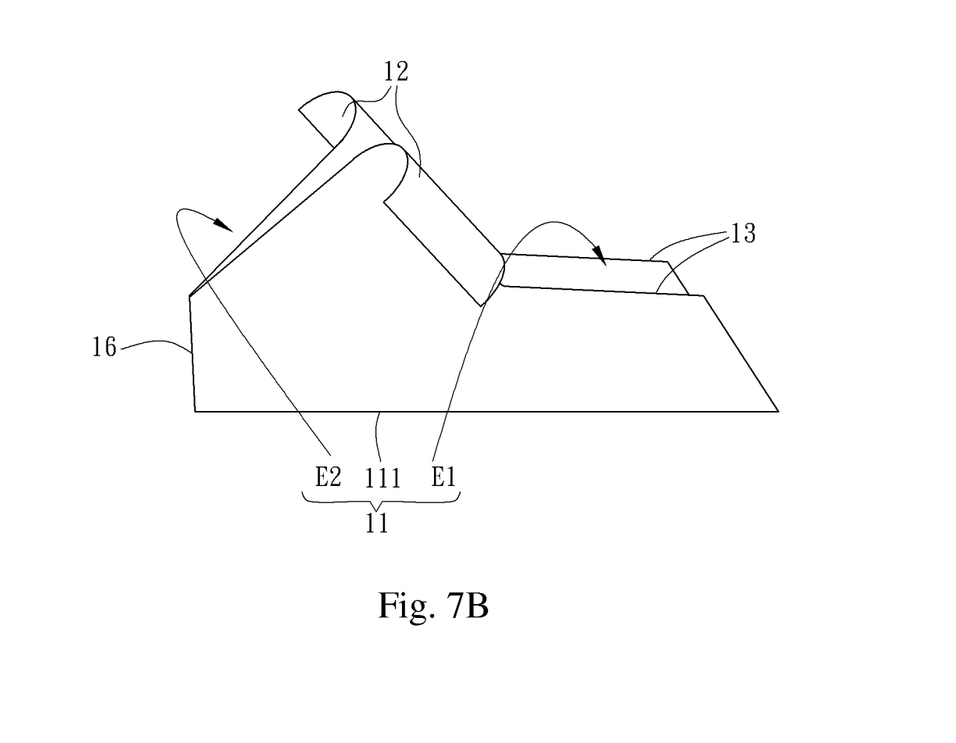

The portable urination device 10 further can include a block portion 16. The block portion 16 is disposed between the bottom edge of the two side walls and the first port E1 or the second port E2 to ensure urine can be discharged through the first port E1 or the second port E2 controlled by users. Referring to FIG. 7A, the block portion 16 is disposed between the bottom edge of the side wall and the first port E1. In the normal operation case, urine can be discharged through the second port E2 via the guiding portion 111. In the careless operation case, urine can be blocked by the block portion 16 if urine flows to the first port E1 that caused by errors of angle adjustment. Referring to FIG. 7B, the block portion 16 is disposed between the bottom edge of the side wall and the second port E2 to ensure urine can be discharged through the first port E1.

Figure 8:
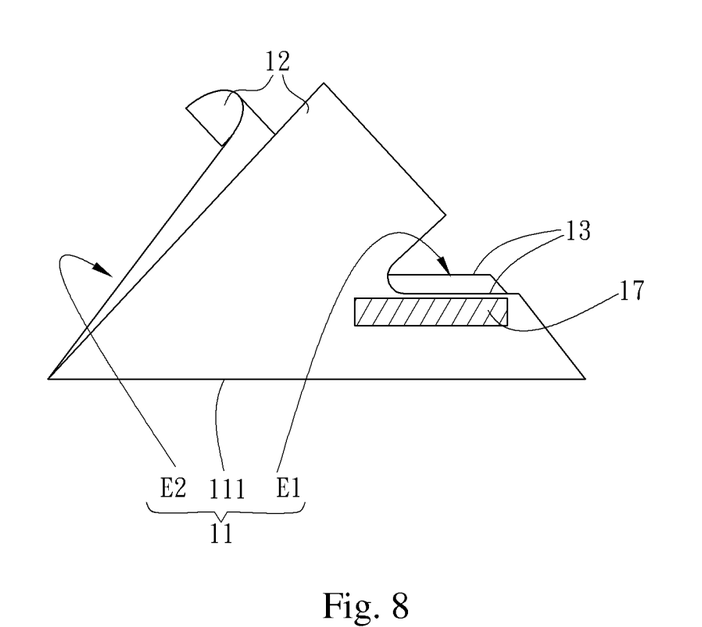
FIG. 8 is a schematic diagram showing one embodiment of the portable urination device having a structure enhanced unit.

Referring to FIG. 8, the portable urination device 10 can include at least a structure enhanced unit 17 disposed on at least one side wall, which is positioned between the first port E1 and the second port E2 to strong the portable urination device 10 so that the portable urination device 10 not easy to deformation in the operation. The structure enhanced unit 17 can be a strip shape or a columnar shape.

Figure 9:
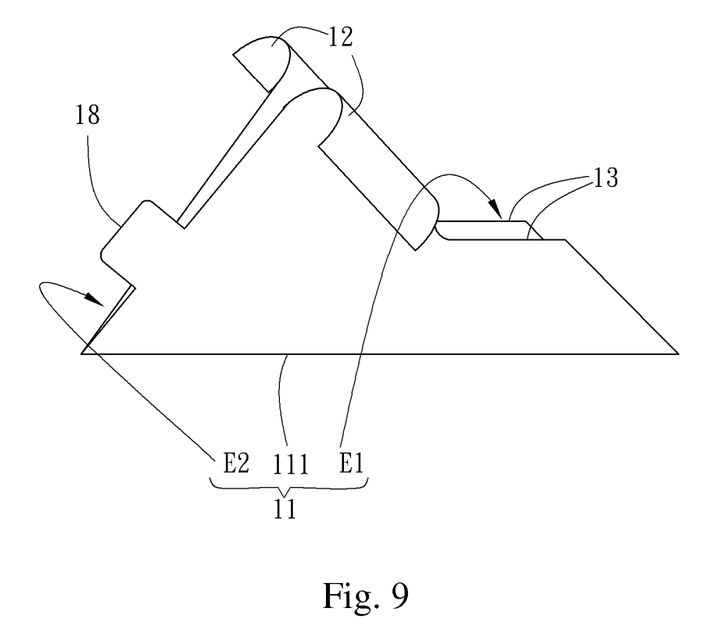
FIG. 9 is a schematic diagram showing one embodiment of the portable urination device having a holding portion.

Referring to FIG. 9, the portable urination device 10 can include at least a holding portion 18 disposed on at least one side wall near the second port E2. The holding portion 18 is for user holding by fingers to control the direction of the second port E2. In the embodiment, the portable urination device 10 includes two holding portions 18. The two holding portions 18 can be integrated forming or adhering to each other.

Even though numerous characteristics and advantages of certain inventive embodiments have been set out in the foregoing description, together with details of the structures and functions of the embodiments, the disclosure is illustrative only. Changes may be made in detail, especially in matters of arrangement of parts, within the principles of the present disclosure to the full extent indicated by the broad general meaning of the terms in which the appended claims are expressed.

What is claimed is:

1. A portable urination device, comprising:
    a guiding body, which has a guiding portion, a first port, and a second port, the first port and the second port are positioned at two ends of the guiding portion, the guiding portion has two side walls, wherein a bottom edge of the two side walls is a closed structure;
    two connection units, which are disposed on the guiding body and are positioned between the first port and the second port; and
    an adhesive layer, which is disposed on at least one portion of one of the connection units such that an user's finger can touch the adhesive layer for steadily operating said portable urination device;
    wherein a receiving portion is positioned at the first port near the two connection units and an open structure is positioned distant from the bottom edge of the two side walls of the guiding body.

2. The portable urination device according to claim 1, wherein at least one of the connection units is a foldable wing extended from one of the side walls, a junction of the foldable wing, the side wall, and the receiving portion are arcuated.

3. The portable urination device according to claim 1, further comprises at least an assist connection unit attached to at least one of the connection units.

4. The portable urination device according to claim 1, wherein an angle exists between an extended line of the top edge of the connection unit and an extended line of the bottom edge of the side wall, and the angle is an obtuse angle.

5. The portable urination device according to claim 1, further comprises a block portion disposed between the bottom edge of the two side walls and the first port or between the bottom edge of the two side walls and the second port.

6. The portable urination device according to claim 1, further comprises at least a structure enhanced unit disposed on at least one of the two side walls, and between the first port and the second port.

7. The portable urination device according to claim 1, further comprises at least a holding portion extended from at least one of the two side walls near the second port.

8. The portable urination device according to claim 1, further comprises a striped adhesive layer disposed on a part of the connection units, wherein the striped adhesive layer is approximately parallel to an extended line of the bottom edge of the two side walls.

9. The portable urination device according to claim 1, wherein an extended line of the top edge of the receiving portion is about parallel to an extended line of the bottom line of the bottom edge of the two side walls.

10. The portable urination device according to claim 1, wherein an angle exists between an extended line of the top edge of at least one of the connection unit and an extended line of the top edge of the receiving portion, and the angle is an obtuse angle.

\* \* \* \* \*